United States Patent [19]

Barr

[11] 4,258,002

[45] Mar. 24, 1981

[54] EXPLOSIVE GAS DETECTOR

[76] Inventor: Thomas A. Barr, 4618 Panorama Dr., Huntsville, Ala. 35801

[21] Appl. No.: 57,710

[22] Filed: Jul. 16, 1979

Related U.S. Application Data

[63] Continuation of Ser. No. 890,372, Mar. 27, 1978, abandoned.

[51] Int. Cl.³ .................... G01N 27/16; G01N 31/12
[52] U.S. Cl. ......................... 422/95; 422/98
[58] Field of Search ............... 23/232 E; 422/83, 94, 422/95, 96, 97, 98, 119

[56] References Cited

U.S. PATENT DOCUMENTS

| | | | |
|---|---|---|---|
| 2,219,540 | 10/1940 | Miller | 422/96 X |
| 2,782,102 | 2/1957 | Howe | 422/96 |
| 2,879,142 | 3/1959 | Jones et al. | 422/96 |
| 3,440,017 | 4/1969 | Palmer | 422/96 |
| 3,553,461 | 1/1971 | Siano et al. | 422/119 X |
| 3,574,555 | 4/1971 | Fertig | 422/96 |
| 3,907,503 | 9/1975 | Betts et al. | 422/67 |

FOREIGN PATENT DOCUMENTS 269053  7/1970  U.S.S.R. .

Primary Examiner—Joseph Scovronek
Attorney, Agent, or Firm—C. A. Phillips

[57] ABSTRACT

An explosive gas detector employing an electrically conductive element which, when powered, changes temperature in the presence of an explosive gas, and a control circuit which senses the increases in temperature and decreases the power input to the element as an inverse function of changes in temperature of the element. The level of electrical power provided the element is indicative of the concentration of explosive gas present.

1 Claim, 2 Drawing Figures

EXPLOSIVE GAS DETECTOR

This is a continuation of application Ser. No. 890,372 filed March 27, 1978, now abandoned.

BACKGROUND OF THE INVENTION

1. Field of the Invention

This invention relates to explosive gas detectors of the catalytic type, and particularly to such a detector wherein means are provided to limit the temperature rise of the catalytic element employed.

2. General Description of the Prior Art

It is known that explosive gas can be detected by an electrically heated wire having on it a catalytic material. Explosive gas causes a reaction with the catalytic material which produces additional heat, and this in turn changes the resistance of the wire. By metering the changes in resistance, as by the employment of an electrical bridge circuit, an indication of the concentration of gas is obtained.

There are several difficulties with this type of detector. A principal one is that the operation of the device depends on elevated temperatures of a catalytic element to provide indications, and the elevated temperatures in turn shorten the life of the element. A second difficulty is that with use, the catalytic element changes character, and this requires recalibration of the detector. A third difficulty is that at high levels of gas concentration, there is a tendency for the device to provide a lower than actual indication of gas, this occurring because of a thermal equilibrium which sometimes arises by virtue of a balance between reaction caused heating of the element and radiation given off by the element. A fourth difficulty is that when operated at higher temperatures, the catalytic element has a tendency to fail in the presence of significant vibrations, and this is particularly a problem when a detector is used on or near mining machinery, as in a coal mine.

It is the object of this invention to overcome the above and other difficulties and to provide an improved explosive gas detector which is both accurate and has a long operating life.

SUMMARY OF THE INVENTION

In accordance with this invention, an explosive gas detector would be constructed wherein power to a catalytic type sensor is controllably varied as a function of temperature and the sensor held at a relatively constant and lower temperature. Gas concentration is measured by monitoring power furnished the sensor, which may be measured by detecting both current and voltage or by detecting voltage across or current through the sensor and by calibrating the detection or monitoring instrument to take into account anticipated change in sensor resistance at different operating levels.

DETAILED DESCRIPTION OF THE DRAWINGS

Figure 1:
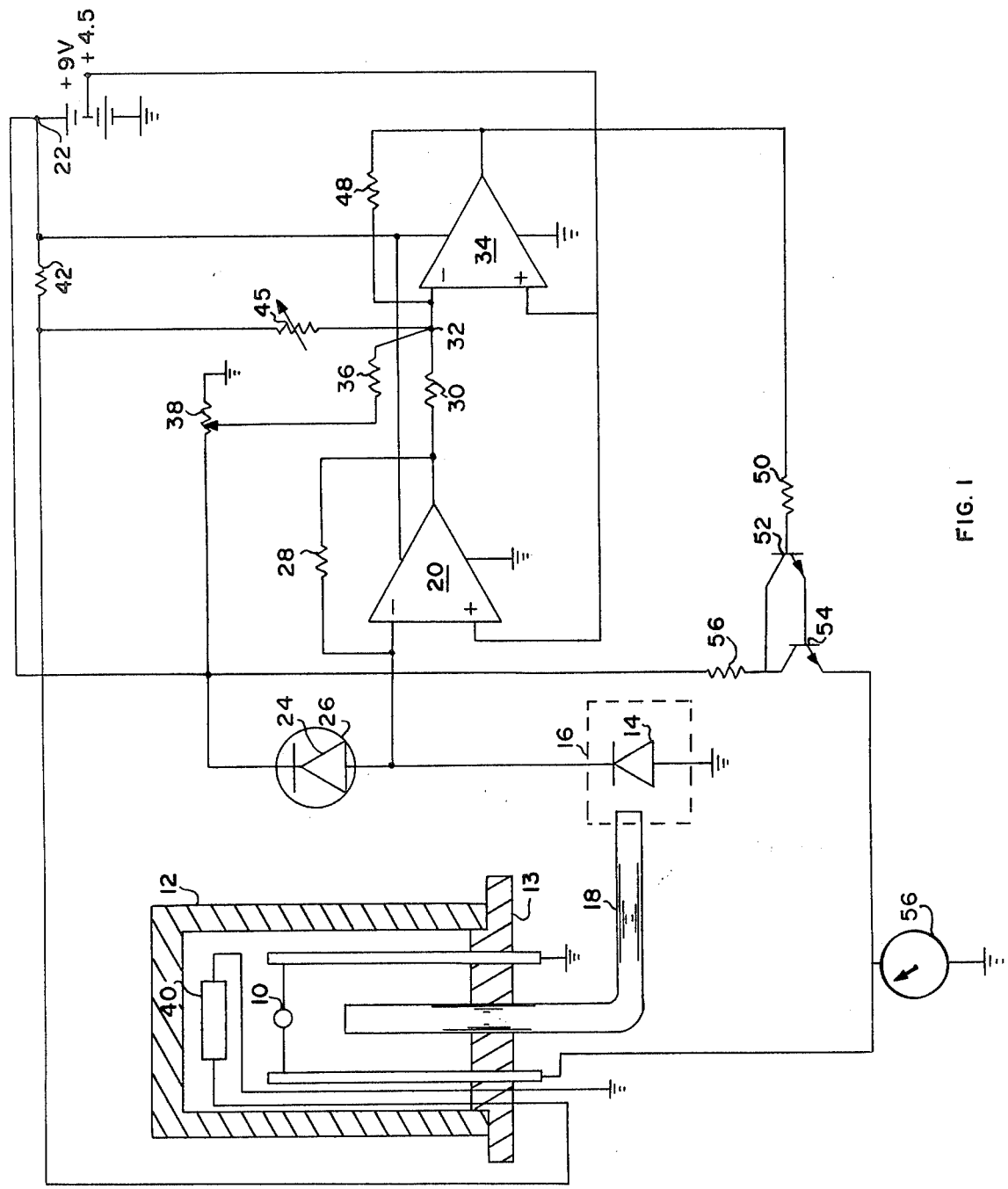
FIG. 1 is a schematic illustration of the structure and electrical system of the invention.

Referring to FIG. 1, a catalytic element 10 is employed as an explosive gas sensor. It is conventional, being formed of a resistance heating member (e.g., platinum wire) covered by a conventional coating containing palladium which produces increased temperature in the presence of explosive gas. Catalytic element 10 is housed in a porous but light-tight metal cover 12 on a base 13, which housing serves several purposes. One, being light-tight, it prevents stray light from interfering with the operation of the system. Second, if a spark should occur from the catalytic element, the spark would be contained. Third, the housing keeps air from being blown over the element, which might cause excessive cooling of it and interfere with accuracy; that is, while atmosphere may slowly enter through the pores of the wall of the housing, it may not enter with any significant velocity.

The heat state of catalytic element 10 is manifested by light emission which is optically sensed by photodiode 14. The photodiode itself is heat isolated from element 10, being positioned in a light-tight enclosure 16, light being furnished it from element 10 by means of fiber optics 18. This isolation is desirable to prevent overheating of photodiode 14 which would adversely affect its sensitivity. Photodiode 14 is electrically connected between the minus input of operational amplifier 20 and ground and is biased from bias source 22 through a second and like photodiode 24, the latter being encased in an opaque housing 26. Having a like electrical resistive-temperature characteristic, photodiode 24 functions as a temperature compensation impedance to maintain a more constant voltage across photodiode 14 (for the same light input) despite changes in ambient temperature. A potential of $4\frac{1}{2}$ volts positive (with respect to a reference ground) from bias source 22 is applied to the plus input of operational amplifier 20, and the output of amplifier 20 is connected to its negative input by feedback resistor 28 to effect a desired amplifier current gain.

The output of amplifier 20 is connected through resistor 30 to a summing junction 32 connected to the negative input of operational amplifier 34. A second input to summing junction 32 is provided through resistor 36 which is connected to an adjustable voltage tap on potentiometer 38, in turn connected between the +9 volts and ground terminals of bias source 22. In this manner, an adjustable operating level for amplifier 32 is provided, and it functions as a power level setting adjustment for element 10, as will be further explained. A third input is provided to summing junction 32 by a temperature compensation circuit wherein thermistor 40, located within housing 12, is connected through load resistor 42 between the +9 volts terminal and ground of bias source 22. Changes in voltage across resistor 48, with temperature produced changes in resistance of thermistor 40, are coupled through variable resistor 45 to summing junction 32. Adjustment of variable resistor 38 provides a means of coupling a selected degree of the voltage change occurring across resistor 38 to the summing junction, and thus provides a means of adjusting the system for minimum drift with temperature change in housing 12.

A reference bias for amplifier 34 is provided by connecting the plus input terminal of the amplifier to the $4\frac{1}{2}$ volts tap of bias source 22. The gain of amplifier 34 is set at approximately 10 by feedback resistor 48 connected between the output and negative input of the amplifier.

Amplifier 34 drives, through resistor 50, the base input of transistor 52 which is direct coupled through its emitter and collector to the base-collector terinals of power transistor 54. The collector of both transistors, transistors 50 and 54, is connected through resistor 56 to the +9 volts terminal of source 22, and the emitter of transistor 54 is connected through catalytic element 10 to ground. Thus, transistor 54, via the signal flow just described, controls the current flow through catalytic element 10.

To examine the operation of the system, assume that operating biases are applied to the circuit as shown, and as a result, catalytic element 10 is applied a desired operating level of current, this being set by potentiometer 38. As described, the ultimate control voltage on transistor 54 will be derived from a combination of light sensed by photodiode 14 from catalytic element 10, a temperature responsive signal from thermistor 40 as adjusted by variable resistor 45 and the power level setting of potentiometer 38. The output of potentiometer 38 would be adjusted with no explosive gas present and would be set at a minimum current level for operation of catalytic element 10. At this operating level, percent gas (e.g., methane) meter 56, an analog or digital voltage sensing meter connected across element 10, would be calibrated to provide a zero indication (e.g., full scale reading of an analog volt meter) of percent gas.

Assume next that the device is placed in an explosive gas environment and that the gas permeates through housing 12 and comes in contact with catalytic element 10. As a result, the element will increase its heat level, and this will be manifested in increased level of light emission. This increase in light emission is sensed, through fiber optic 18 by photodiode 14, and as a result, the resistance of photodiode 14 decreases. The decrease causes a reduced voltage to appear on the minus input of amplifier 20, and then through successive amplifications by amplifier 32 and transistor 52, a reduced voltage would be applied to the base of power transistor 54 which would then reduce current flow to catalytic element 10 until its operating level is reduced to the state existing prior to exposure to the gas, at which point the system will reach an equilibrium manifested by a reduction in applied power to catalytic element 10. This decrease, sensed by meter 56, indicates the responsive concentration of gas present which produced the changed power operating level. In order to provide an accurate readout of percentages of gas present, meter 56 would, of course, be calibrated prior to field use by the employment of calibrated samples of gas concentrations. Once calibrated, calibration is monitored over extended periods of usage.

Figure 2:
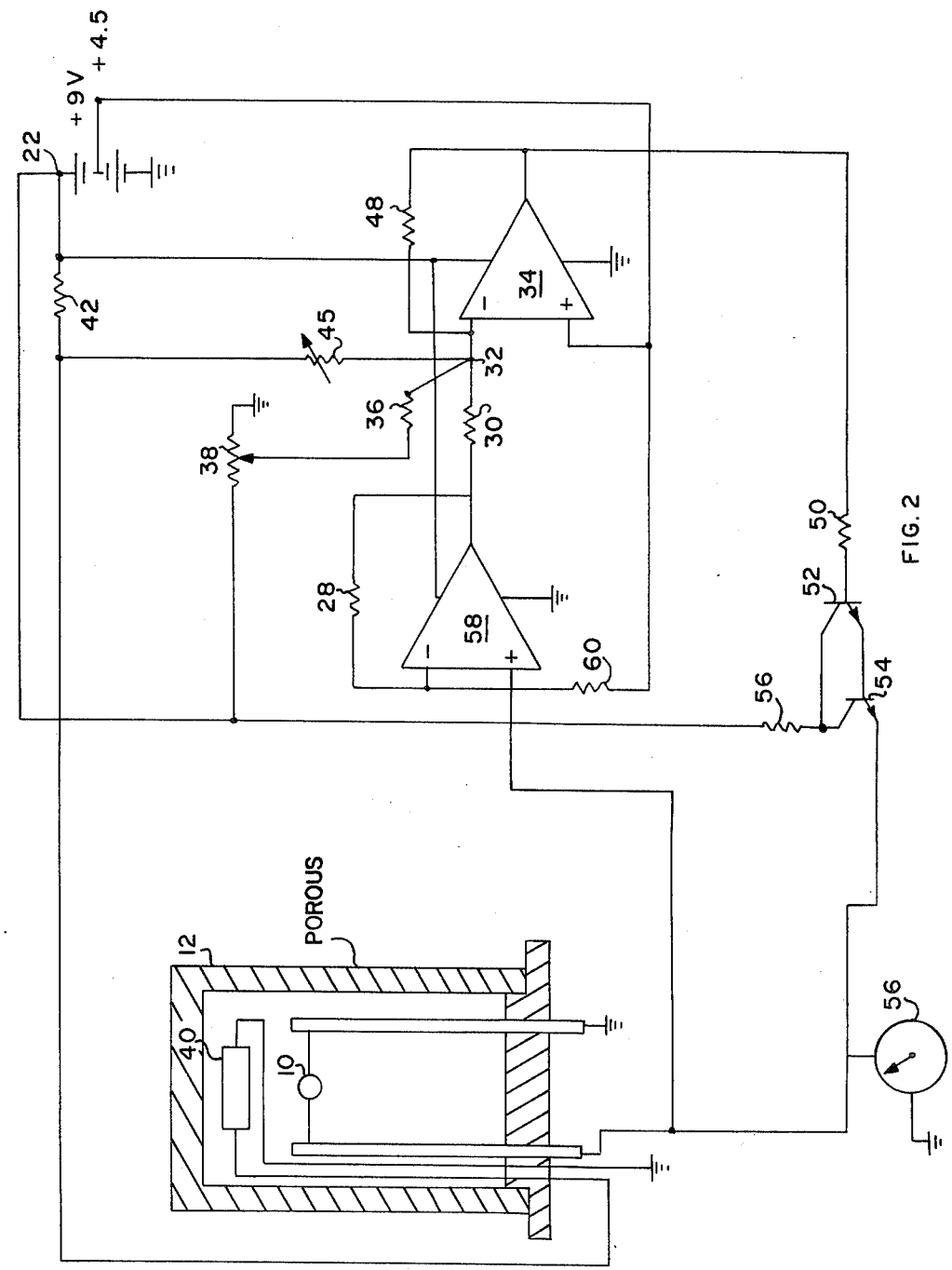
FIG. 2 is a schematic illustration of an alternate embodiment of the invention.

FIG. 2 illustrates an embodiment of the invention wherein changes in temperature of catalytic element 10 are sensed by directly proportional changes in resistance of the catalytic element. Thus, as shown, the voltage across catalytic element 10, responsive to the level of impedance of catalytic element 10, is applied to the plus input of operational amplifier 58. A reference input, one-half supply voltage, is applied through resistor 60 to the negative input of amplifier 58, and the values of resistors 28 and 60 are adjusted to provide a desired amplifier gain.

Amplifier 58 provides an output signal which increases with increased temperature of catalytic element 10, as represented by increases in impedance with increased temperature of the element. This signal is applied through resistor 30 to summing junction 32, and thus to the negative input of operational amplifier 34 where it is summed with a power level signal from potentiometer 38 and a container temperature compensation signal from thermistor 40, as in the case of the temperature signal from photodiode 14, as shown in FIG. 1. The balance of the circuitry is identical and operates in the same fashion as that shown in FIG. 1.

Having thus described my invention, what is claimed is:

1. An explosive gas detector comprising:
   a container having a gas entrance;
   a source of DC power having a ground reference terminal, a full voltage terminal, and a fractional voltage terminal;
   impedance means positioned in said container and having first and second terminals, and comprising:
     a conductor which varies in impedance directly with temperature,
     a catalytic material coated on said conductor, which material increases in temperature in the presence of an explosive gas, and
     said first terminal being connected to said reference terminal of said power source;
   a transistor having its collector and emitter connected in series between said full voltage terminals of said power source and said second terminal of said impedance means;
   first amplification means comprising an operational amplifier having its non-inverting input connected to said second terminal of said impedance means and its inverting input connected to said fractional voltage terminal of said power source;
   a container temperature responsive circuit comprising a thermistor positioned within said container and a resistor connected in series with said thermistor between said reference terminal and one of said power terminals of said power source;
   a summing circuit comprising:
     a summing junction,
     a first input to said summing junction comprising a resistor connected between the output of said first operational amplifier and said summing junction,
     a second summing junction input comprising a container temperature responsive input including a variable resistor, one terminal of said variable resistor being connected to said summing junction, and the other terminal being connected through said resistor of said temperature responsive circuit to one of said power terminals of said power source, and
     a third input to said summing junction comprising an operating level circuit, in turn including a second variable resistor connected between said junction and one of said power terminals of said power source;
   a second operational amplifier, its inverting input being connected to said summing junction, and its non-inverting input being connected to said fractional voltage terminal of said power source;
   drive means connected to the output of said second operational amplifier for applying a drive signal to the base of said transistor for controlling the impedance of said transistor as a direct function of current flow through said impedance means, whereby the voltage applied to said impedance means is decreased as a function of explosive gas sensed by said catalytic material; and
   indication means responsive to the voltage across said impedance means for indicating the quantity of gas present.

* * * * *